(12) United States Patent
Pschorn et al.

(10) Patent No.: US 8,512,512 B2
(45) Date of Patent: Aug. 20, 2013

(54) SYSTEM AND METHOD FOR PREEXTRACTION OF HEMICELLULOSE THROUGH USING A CONTINUOUS PREHYDROLYSIS AND STEAM EXPLOSION PRETREATMENT PROCESS

(75) Inventors: Thomas Pschorn, Sherbrooke (CA); Namhee Shin, Clifton Park, NY (US); Bertil Stromberg, Diamond Point, NY (US)

(73) Assignee: Andritz Inc., Glen Falls, NY (US)

( * ) Notice: Subject to any disclaimer, the term of this patent is extended or adjusted under 35 U.S.C. 154(b) by 0 days.

(21) Appl. No.: 13/280,888

(22) Filed: Oct. 25, 2011

(65) Prior Publication Data
US 2012/0041186 A1 Feb. 16, 2012

Related U.S. Application Data

(62) Division of application No. 12/389,020, filed on Feb. 19, 2009, now Pat. No. 8,057,639.

(60) Provisional application No. 61/032,115, filed on Feb. 28, 2008.

(51) Int. Cl.
*D21C 3/26* (2006.01)
*C08B 1/00* (2006.01)

(52) U.S. Cl.
USPC ............. 162/19; 162/21; 162/237; 536/56; 536/128; 435/162

(58) Field of Classification Search
USPC ....... 162/19, 21, 237; 536/56, 128; 422/189; 435/162
See application file for complete search history.

(56) References Cited

U.S. PATENT DOCUMENTS

| | | |
|---|---|---|
| 1,922,313 A | 8/1933 | Mason |
| 2,615,906 A | 10/1952 | Stanton |

(Continued)

FOREIGN PATENT DOCUMENTS

| | | |
|---|---|---|
| EP | 2 003 241 A2 | 12/2008 |
| WO | 2006034590 A1 | 4/2006 |

(Continued)

OTHER PUBLICATIONS

Johanna Soderstrom "Optimisation of Two-Step Steam Pretreatment of Softwood for Bioethanol Production", p. 60 (Lund University) Sweden, 2004.

(Continued)

*Primary Examiner* — Jacob T Minskey
(74) *Attorney, Agent, or Firm* — Nixon & Vanderhye P.C.

(57) ABSTRACT

A method including: pretreating biomass feed stock in a first pressurized reactor, wherein the feed stock undergoes hydrolysis in the first pressurized reactor; discharging the feed stock from the first pressurized reactor to a pressurized sealing device having a first pressurized coupling to a feedstock discharge port of the first pressurized reactor; maintaining a vapor phase in the first pressurized reactor by injecting steam; washing the feed stock; draining dissolved hemi-cellulosic material extracted from the feed stock; discharging the feed stock from the pressurized sealing device through a second pressurized coupling to a second pressurized reactor; in the second pressurized reactor, infusing cells of the feed stock with steam or water vapor, and rapidly releasing the pressure applied to the feed stock to cause steam expansion in the cells of the feed stock and refine the feed stock.

21 Claims, 8 Drawing Sheets

(56) References Cited

U.S. PATENT DOCUMENTS

| | | | |
|---|---|---|---|
| 2,616,802 | A | 11/1952 | Alphonse et al. |
| 2,681,871 | A | 6/1954 | Wallace |
| 2,961,041 | A | 11/1960 | Lesniak |
| 4,163,687 | A | 8/1979 | Mamers et al. |
| 4,237,226 | A | 12/1980 | Grethlein |
| 4,316,748 | A | 2/1982 | Rugg et al. |
| 4,427,453 | A * | 1/1984 | Reitter ................................ 127/1 |
| 4,612,286 | A | 9/1986 | Sherman et al. |
| 4,708,746 | A | 11/1987 | Hinger |
| 4,966,650 | A | 10/1990 | DeLong et al. |
| 5,123,962 | A * | 6/1992 | Komuro et al. .......... 106/164.01 |
| 5,262,003 | A | 11/1993 | Chupka et al. |
| 5,338,366 | A | 8/1994 | Grace et al. |
| 5,411,594 | A | 5/1995 | Brelsford |
| 5,454,911 | A | 10/1995 | Rafferty |
| 5,617,975 | A | 4/1997 | Johanson et al. |
| 5,628,873 | A | 5/1997 | Johanson et al. |
| 5,753,075 | A | 5/1998 | Stromberg et al. |
| 5,865,898 | A | 2/1999 | Holtzapple et al. |
| 5,876,505 | A | 3/1999 | Klyosov et al. |
| 5,916,780 | A | 6/1999 | Foody et al. |
| 6,090,595 | A | 7/2000 | Foody et al. |
| 6,409,841 | B1 | 6/2002 | Lombard |
| 6,423,145 | B1 | 7/2002 | Nguyen et al. |
| 6,660,506 | B2 | 12/2003 | Nguyen et al. |
| 7,189,306 | B2 | 3/2007 | Gervais |
| 7,937,851 | B2 | 5/2011 | Rajagopalan et al. |
| 2002/0117167 | A1 | 8/2002 | Schmidt et al. |
| 2007/0148751 | A1 | 6/2007 | Griffin et al. |
| 2007/0284068 | A1 | 12/2007 | Francis et al. |
| 2007/0298477 | A1 | 12/2007 | Kratochvil et al. |
| 2008/0142176 | A1 | 6/2008 | van Heiningen et al. |
| 2008/0142181 | A1 | 6/2008 | Sabourin |
| 2009/0035826 | A1 | 2/2009 | Tolan et al. |
| 2010/0041119 | A1 | 2/2010 | Christensen et al. |

FOREIGN PATENT DOCUMENTS

| | | |
|---|---|---|
| WO | 2007/051269 | 5/2007 |
| WO | 2007/051269 A1 | 5/2007 |
| WO | 2008/026932 A1 | 3/2008 |
| WO | 2008/137639 A1 | 11/2008 |

OTHER PUBLICATIONS

"Continual Shrinking-Bed Reactor Boosts Biomass Ethanol", NREL Research Brief (Apr. 1997).

Renata Bura, "Bioconversion of Forest Biomass to Ethanol", College of Forest Resources, "Bioenergy Group", Oct. 20, 2008.

Y. Boluk, "Lignocellulosic Biomass Processing for Bioethanol", Bioconversion and Bioproducts Forest Products Business Unit Alberta Research Council, Nov. 1, 2006.

European Search Report mailed Aug. 19, 2009 for PCT/US2009/035273.

Yoshiyuki Sasaki, "Conversion of Woody Biomass to Chemicals", Biomass Asia Workshop, Jan. 20, 2005, 21 pages.

Andritz, "Mechanical Pulp", Oct. 2006, 6 pages.

"Understanding Biomass As A Source of Sugars and Energy", Energy Efficiency and Renewable Energy, pp. 1-3, printed Feb. 26, 2008.

"ABC's of Biofuels", Energy Efficiency and Renewable Energy, pp. 1-5, printed Feb. 26, 2008.

Diane Greer, "Creating Cellulosic Ethanol: Spinning Straw Into Fuel", BioCycle, May 2005 eNews Bulletin, pp. 1-9, printed Feb. 26, 2008.

Anders Wingren et al., "Process Considerations and Economic Evaluation of Two-Step Steam Pretreatment for Production of Fuel Ethanol from Softwood", Biotechnol. Prog. 2004, 20, 1421-1429.

Q.A. Nguyen et al., "Dilute Acid Pretreatment of Softwoods Scientific Note", Applied Biochemistry and Biotechnology, vol. 70-72, 1998, pp. 77-87.

Yang, et al. "A Kinetic Study of Xylan Solubility and Degradation during Corncob Steaming." Biosystems Engineering (2006) 93 (4)I 375-382, doi:10.1016/j.biosystemseng.2006.01.006.

Taherzadeh, et al. "Acid-Based Hydrolysis Processes for Ethanol from Lignocellulosic Materials: A Review." BioResources 2(3), 472-499.

Kim, et al. "Cellulose Hydrolysis Under Extremely Low Sulfuric Acid and High-temperature Condition." Applied Biochemistry and Biotechnology, vol. 91-93, 2001.

Lloyd, et al. "Combined Sugar Yields for Dilute Sulfuric Acid Pretreatment of Corn Stover Followed by Enzymatic Hydrolysis of the Remaining Solids." Bioresource Technology 96 (2005) 1967-1977.

Martin, et al. "Dilute Sulfuric Acid Pretreatment of Agricultural and Agro-Industrial Residues for Ethanol Production." Applied Biochemistry and Biotechnology, vol. 136-140, 2007.

Schell, et al. "Dilute-Sulfuric Acid Pretreatment of Corn Stover in Pilot-Scale Reactor." Applied Biochemistry and Biotechnology, vol. 105-108, 2003.

Ohgren, et al. "Effect of hemicellulose and lignin removal on enzymatic hydrolysis of steam pretreated corn stover." Bioresour. Technol. (2006), dio:10.1016/j.biotech.2006.09.003.

Tucker, et al. "Effects of Temperature and Moisture on Dilute-Acid Steam Explosion Pretreatment of Corn Stover and Cellulase Enzyme Digestibility." Applied Biochemistry and Biotechnology vol. 105-108, 2003.

Conner, et al. "Kinetic Model for the Dilute Sulfuric Acid Saccharification of Lignocellulose." Journal of Wood Chemistry and Technology, 5(4), 461-489, 1985.

Lee, et al. "Kinetic and Modeling Investigation to Provide Design Guidelines for the NREL Dilute-Acid Process Aimed at Total Hydrolysis/Fractionation of Lignocellulosic Biomass." Aug. 2004, NREL/SR-510-36392.

Aden, et al. "Lignocellulosic Biomass to ethanol Process Design and Economics Utilizing Co-Current Dilute Acid Prehydrolysis and Enzymatic Hydrolysis for Corn Stover." Task No. BFP2.A410, Jun. 2002, NERL/TP-510.

Grohmann, et al. "Optimization of Dilute Acid Pretreatment of Biomass." Biotechnology and Bioengineering Symp. No. 15 (1985).

McMillan. "Processes for Pretreating Lignocellulosic Biomass: A Review." NREL/TP-421-4978, Nov. 1992.

Mok, et al. "Productive and Parasitic Pathways in Dilute Acid-Catalyzed Hydrolysis of Cellulose." Ind. Eng. Chem. Res., vol. 31, No. 1, 1992.

Zhang, et al. "Fractionating Recalcitrant Lignocellulose at Modest Reaction Conditions." Biotechnol Bioeng, Jun. 1, 2007, vol. 97, No. 2, pp. 214-223.

* cited by examiner

SYSTEM AND METHOD FOR PREEXTRACTION OF HEMICELLULOSE THROUGH USING A CONTINUOUS PREHYDROLYSIS AND STEAM EXPLOSION PRETREATMENT PROCESS

CROSS RELATED APPLICATION

This application is a divisional of U.S. Non-Provisional Utility application Ser. No. 12/389,020, filed Feb. 19, 2009, and claims the benefit of U.S. Provisional Utility Patent Application 61/032,115, filed Feb. 28, 2008, the entirety of both of these applications are incorporated by reference.

BACKGROUND OF THE INVENTION

The present invention relates to pre-treatment of cellulosic biomass feed stocks, such as agricultural residues (including stalks, stover and hulls), straws and grasses, forest and sawmill residues (including wood chips and shredded thinnings). In particular, the invention relates to pre-hydrolysis and steam explosion pretreatment to extract carbon sugars from the biomass feed stocks.

High pressures and/or high temperatures are typical in pre-treatments used to generate alcohols, e.g. ethanol, from cellulosic feed-stocks. In these conventional pre-treatments, some C5 sugars are converted to components which inhibit the alcohol fermentation of C6 sugars in the fermentation step following pre-treatment. Removing these inhibiting components, such as aldehydes (e.g., HMF, furfural, and formaldehyde), monomeric phenolics (e.g., vanillin and coniferylaldehyde), acids (e.g., formic acid) and other inhibitors should increase the alcohol yield in the C6 fermentation step following pretreatment.

SUMMARY OF THE INVENTION

A system has been developed for pretreating cellulosic biomass feed stock including: a system for pretreating cellulosic biomass feed stock comprising: a first pressurized reactor receiving the feed stock, wherein the feed stock undergoes hydrolysis in the first pressurized reactor; a sealing device having a first pressurized coupling to a feedstock discharge port of the first pressurized reactor, and a second pressurized coupling to a second pressurized reactor; a drain for a liquid including dissolved hemi-cellulosic material extracted from the feed stock in at least one of the first pressurized reactor and the sealing device; the second pressurized reactor assembly receiving the pressurized feed stock from the sealing device at a pressure substantially greater than the pressure in the first pressurized reactor, and an expansion device downstream of the second pressurized reactor assembly, wherein the expansion device rapidly releases the pressure of the feed stock discharged from the second pressurized reactor such that the feed stock undergoes a steam explosion reaction, wherein the first reactor and the second reactor each include a steam phase receiving direct steam heating and reacting or heating the feedstock.

In another embodiment, the system for pretreating cellulosic biomass feed stock may comprise: a first pressurized reactor receiving the feed stock, wherein the feed stock undergoes hydrolysis in the first pressurized reactor at a gauge pressure in a range of 1.5 bar gauge to 6 bar gauge or higher, and at a temperature of at least 110 degrees Celsius; a sealing and extraction device having a first pressurized coupling to a feedstock discharge port of the first pressurized reactor and a second pressurized coupling to a second pressurized reactor; a wash stage introducing a wash liquid into the feed stock in at least one of the first pressurized reactor and the sealing extraction device; a drain for removing a liquid including dissolved hemi-cellulosic material extracted from the feed stock in at least one of the first pressurized reactor and the sealing and extraction device; the second pressurized reactor assembly receiving the pressurized feed stock from the sealing and extraction device and infusing a steam and water vapor into the feed stock in the second pressurized reactor, wherein the reactor assembly applies a gauge pressure to the feed stock in a range of 8 bar gauge to 25.5 bar gauge, and the second pressurized reactor assembly having a pressurized discharge coupled to a discharge conduit, and an expansion device downstream of the second pressurized reactor assembly, wherein the expansion device rapidly releases the pressure of the feed stock discharged from the second pressurized reactor such that the feed stock undergoes a steam explosion reaction.

A method has been developed pretreating cellulosic biomass feed stock comprising: pretreating the feed stock in a first pressurized reactor, wherein the feed stock undergoes hydrolysis in the first pressurized reactor; discharging the feed stock from the first pressurized reactor to a pressurized sealing device having a first pressurized coupling to a feedstock discharge port of the first pressurized reactor; maintaining a vapor phase in the first pressurized reactor by injecting steam into the first pressurized reactor, wherein the injected steam provides heat energy to the feedstock in the first pressurized reactor; washing the feed stock in a downstream region of the first pressurized reactor or the pressurized sealing device; draining a liquid including dissolved hemi-cellulosic material extracted from the feed stock from at least one of the first pressurized reactor and the pressurized sealing device; discharging the feed stock from the pressurized sealing device through a second pressurized coupling to a second pressurized reactor, wherein the feed stock is maintained at a higher pressure in the second pressurized reactor than in the first pressurized reactor; in the second pressurized reactor, infusing cells of the feed stock with steam or water vapor by injecting steam or water vapor into the second pressurized reactor, and rapidly releasing a pressure applied to the feed stock to cause steam expansion in the cells of the feed stock and the feed stock may be refined.

DETAILED DESCRIPTION OF THE INVENTION

Figure 1:
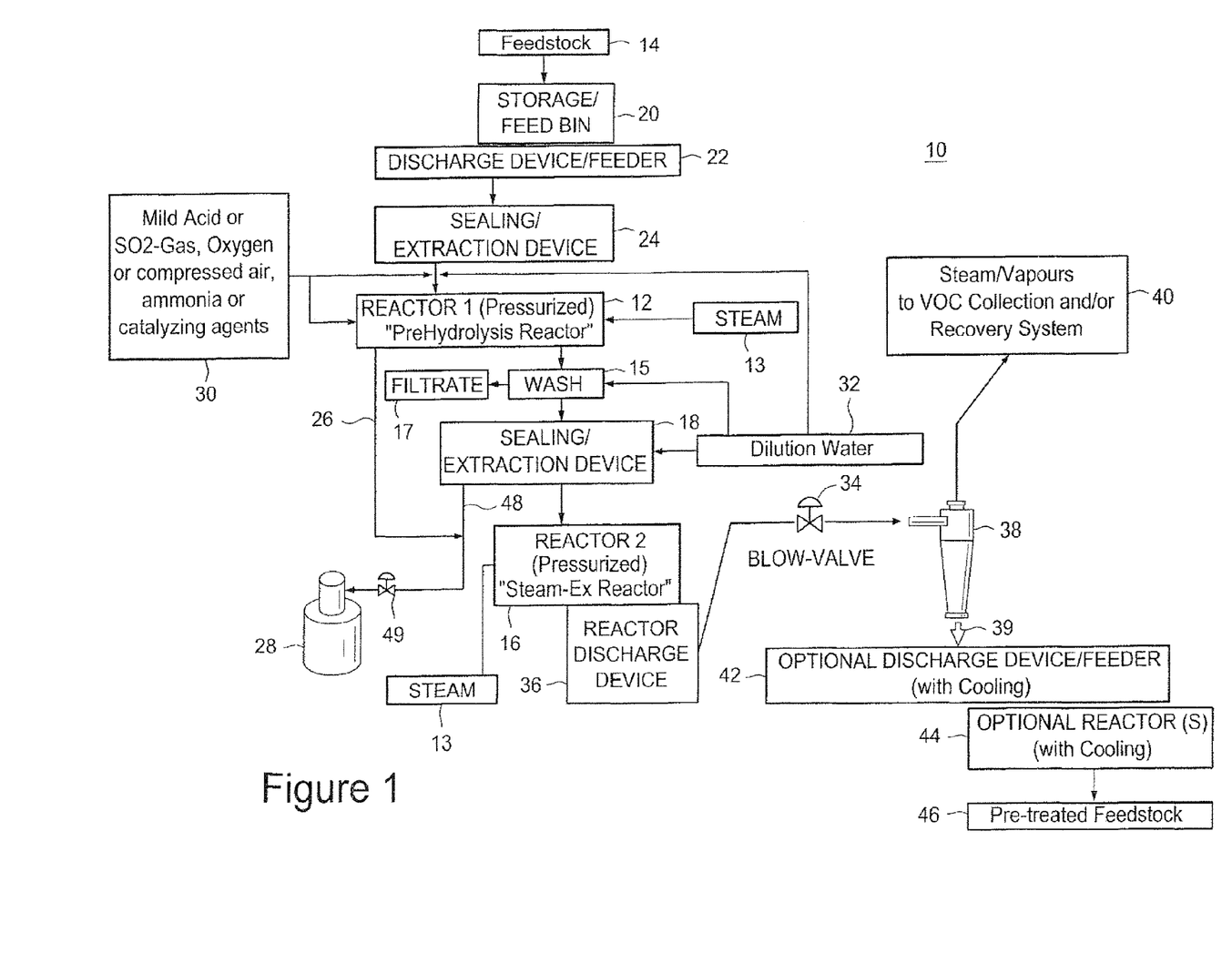
FIG. 1 depicts a schematic diagram of a flow through a two reactor process for pre-treatment of cellulosic biomass feed stock.
Figure 2:
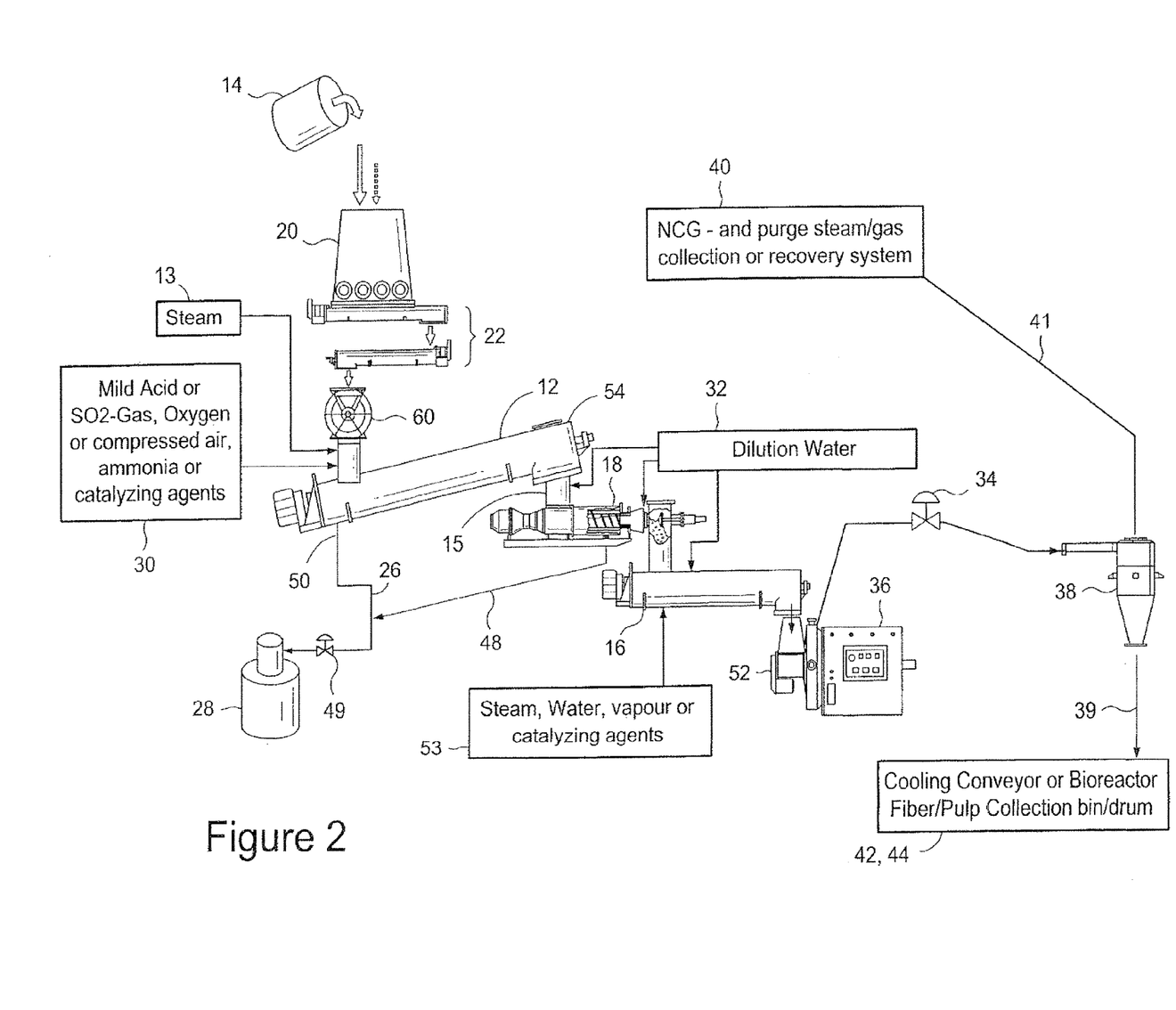
FIG. 2 depicts a reactor system with an inclined first reactor with an input lower than the discharge and a horizontal second reactor.

FIG. 1 shows a flow sketch of a cellulosic biomass feed stock pre-treatment process 10 having a first pressurized reactor 12 to hydrolyze and dissolve hemi-cellulose from feed stock 14. The hemi-cellulose is dissolved into a liquid to extract C5-sugars before the feed stock flows to a second pressurized reactor 16 to cook the remaining cellulose in the feed stock. A pressurized seal 18 allows for a continuous flow of pressurized feed stock directly from the first reactor 12 to the second reactor 16.

The feed stock 14 may be a cellulosic biomass material such as agricultural residues (e.g., stalks, stover and hulls), straws, grasses, and forest and sawmill residues (e.g., wood chips and shredded thinnings). The feed stock 14 is fed to a storage bin 20 where the stock is maintained, at least temporarily, at atmospheric pressure. The storage bin may provide pre-steaming to heat the feed stock. From the storage bin 20, the feed stock is carried by a conveyor 22 to a pressure sealing device 24, such as a rotary valve, plug screw feeder or a MSD Impressafiner® sold by Andritz Inc. of Glens Falls, N.Y., USA. The pressure sealing device 24 serves as an input portal for the feed stock to the first pressurized reactor 12.

In the first pressurized reactor 12, the cellulosic biomass feed stock is pretreated using hydrolysis, e.g., pre-hydrolysis or auto-hydrolysis, to extract carbon sugars, preferably C5-sugars, from the feed stock prior to the second pressurized reactor 16. The first pressurized reactor may be horizontal, inclined or vertical. The hydrolysis cooking in the first reactor 12 may be a continuous process in which the feed stock continuously enters, flows through and is discharged from the reactor 12 to the pressurized seal 18 and through the second reactor 16.

In the first pressurized reactor 12, hemi-cellulose, which is mainly 5-carbon sugars (referred to herein as "C5-sugars"), is dissolved and hydrolyzed. The hemi-cellulose is extracted in a liquid from the first pressurized reactor 12 via a conduit 26 extending from the reactor 12 to a blow down tank or drum 28.

Hemi-cellulose in soft-woods is mostly gluco-mannan which is dissolved and hydrolyzed in pre-hydrolysis and auto-hydrolysis processes of the first reactor 12. The hemi-cellulose in, for example, hard-woods, cereal straws and grasses may dissolve and be hydrolyzed in the acid solution in the first reactor 12 (optionally in the presence of catalyst(s)) into low molecular weight C5-sugars, such as xylose and arabinose, and to a certain extent into amorphous C6-sugars. The low molecular weight C5 and amorphous C6 sugars are dissolved in the reactor 12 and drained as a liquor (liquid) from the reactor 12 to pipe 26. Examples of C5-sugar by-products that are preferably removed as liquor from the feed stock in the first reactor 12 include: aldehydes (HMF, furfural and formaldehyde), monomeric phenolics (vanillin and coniferylaldehyde) and acids (such as acetic acid and formic acid). Removal of these C5-sugar by-products is desirable as they, or their reaction by products, could inhibit the fermentation of C6-sugars if not separated in the first reactor 12 from the feed stock.

In the first pressurized vessel reactor 12, the feed stock may be processed in an acid solution that promotes pre-hydrolysis or auto-hydrolysis to dissolve and hydrolyze the hemi-cellulose in the feed stock to low molecular weight C5-sugars and amorphous C6-surgars. The reactor 12 may not be filled with feed stock to allow for a steam phase in the reactor. The steam phase provides heat energy for the feed stock and to promote the hydrolysis reaction in the feedstock that may be in either or both of the steam phase or a liquid phase of the reactor. The steam to the reactor 12 may be supplied from a steam source 13 which injects steam directly into the reactor at one or more positions of the reactor 12, and preferably near the feedstock inlet of the reactor. The steam may also be injected in the feedstock conveyors 22, 24 immediately upstream of the inlet the reactor 12. Injection of steam upstream of the inlet to the reactor 12 enhances the mixing of steam and the feedstock before the mixture enters the reactor.

Hydrolysis, and particularly pre-hydrolysis and auto-hydrolysis, generally refers to the cooking of the cellulosic biomass feed stock at temperatures of, for example, between 110 degrees Celsius (° C.) and 160° C. or 110° C. to 175° C. at a gauge pressure of 1.5 bar to 6 bar (150 to 600 kilopascals) or 1.5 bar to 10 bar (150 to 1000 kilopascals), for approximately ten (10) minutes to sixty (60) minutes (min.) and preferably 20 to 30 minutes. To promote hydrolysis and provide pressurization, the first pressurized reactor 12 may receive flows of one or more of a mild acid, sulfur dioxide gas ($SO_2$), oxygen, compressed air, ammonia, water, water vapor, steam (for heating and maintaining temperature) and catalyzing agents from sources 30, 13 of each of these compounds. The received flow(s) 30, 13 may be introduced to the first pressurized reactor 12 proximal to where the feedstock enters the reactor and distal from where the feed stock exits the first pressurized vessel. As an alternative to adding acids, the first reactor 12 may utilize auto-hydrolysis conditions such as by using the wood acids released by the feed stock under auto-hydrolysis conditions.

The feedstock may be discharged wet or dry from the first reactor 12. Dilution water or liquor 32 may be optionally added to the first reactor 12 or to the sealing and extraction device 18. Adding dilution water benefits the removal of any dissolved substance from the sealing and extraction device 18, and increases the amount of sugars recovered in the streams flowing through conduits 26 and 48.

Further, a wash stage 15 may be include in or immediately downstream of the first reactor 12 and upstream of the second reactor 16 and preferably upstream of the sealing and extraction device 18 to wash the feedstock with dilution water to, for example, ensure that the hydrolysis reaction has ceased. For example, the wash stage may be located at the flow end of the first reactor 12 or in the sealing and extraction device 18. The wash stage 15 introduces clean water, such as from the dilution water source 32, to the feed stock in a wash zone (see FIG. 7) near the outlet of the first reactor or in the sealing and extraction device 18. The wash water from source 32 may have a temperature of no more than 160 degrees Celsius, no more than 140 degrees Celsius or no more than 110 degrees Celsius. The temperature of the wash water is lower than the temperature in the first reactor 12 to suppress the hydrolysis reaction in the wash zone. The wash zone extracts filtrate 17 from the feed stock through, for example, the drain conduit 48.

The wash stage should be upstream of the steam explosion process, such as upstream of valve 34. It is more economical and efficient to wash the feedstock upstream of the steam explosion process than to wash the feedstock after the steam explosion process. The steam explosion process reduces the particle size of the feedstock and thus increases the specific surface area of the feedstock. The small particles and the resulting large specific surface area increase the difficulty of dewatering and washing feedstock. Washing upstream of the steam explosion process avoids these difficulties because the feedstock particles are relatively coarse and have a smaller specific surface prior to steam explosion.

Because washing feedstock with larger particles is more efficient as compared to washing smaller particles, the washing equipment, such as wash zones, water injectors, filtrate screens and extraction devices, may be less cumbersome and less expensive than the wash equipment needed for washing downstream of the steam explosion process. Similarly, the costs associated with washing, such as costs for providing wash liquid and extracting filtrate, is less if the washing step is upstream of the steam explosion process than if the step is downstream of the process.

The blow-tank 28 collects the dissolved components such as C5-sugars from the hemi-cellulose extracted from the feed stock in the first reactor 12 and the sealing and extraction device 18 via pipes (also referred to as conduits) 26 and 48. The liquid solution of dissolved hemi-cellulose, e.g., C5 sugars, extracted from the reactor 12 may be de-pressurized through a pressure reduction valve 49 in the pipe 48 to the blow-tank or at the discharge of the blow-tank 28. Having been separated from the feed stock and stored in the tank 28, the C5-sugars in the hemi-cellulose may be converted by conventional processes to Xylose for use as food additives, biogas by aerobic and anaerobe fermentation, methyl-furan by high octane oxygenate, and to an aqueous sugar for conversion to alcohols, such as ethanol. The conversion of C5-sugars may use special micro-organisms, e.g., enzymes, to promote the conversion reaction.

For any of the reactor systems in this disclosure, an optional washing apparatus may be included between the first and second reactors to wash the feedstock. The washing apparatus may include an input for a solvent (such as the acid solutions used in the first reactor, water, steam or a combination thereof) to be mixed with the feedstock before or after the removal of the dissolved hemi-cellulose. The solvent may further dissolve hemi-cellulose associated with the feedstock that was not removed after the first removal of the dissolved components. The solvent may be introduced at a temperature or pressure that is below the temperature or pressure of the first reactor. Since the temperature or pressure or both is below that of the first reactor, the solvent has the additional benefit of stopping the chemical reaction(s) induced in the feedstock by the first reactor. The output of the washing apparatus containing solvent with additional hemi-cellulose may be processed separately or may be combined with the previously extracted dissolved component in blow tank 28. The washing apparatus may further comprise additional steam ports and inputs for maintaining the temperature and pressure of the process. The washing apparatus may be incorporated into the first reactor (12), or the sealing extraction device (18) such that additional hardware is not required to implement the washing step. For example, the first reactor or the sealing extraction device may include an input port for the additional solvent for further washing the feedstock. The solvent may be removed using the regular solvent removal ports of the reactor system such as conduit 26 or 48.

After removal of the dissolved hemi-cellulose, the remaining feed stock is discharged from the first reactor 12 to the sealing or extraction device 18. The feed stock remains pressurized and flows from the first reactor to the sealing and extraction device 18. The sealing and extraction device 18 conveys the feed stock from the first reactor 12 to the second reactor 16. The sealing or extraction device 18 may increase the pressure applied to the feed stock to a level above the pressure in the first reactor 12 and to a level suitable for a steam explosion that will occur after the second reactor 16. The second pressurized reactor may include a horizontal or conical reactor vessel.

The pressurized sealing and extraction device 18 may be a (MSD) Impressafiner®, an extruder like screw device, or a plug screw feeder or a similar unit which squeezes the pre-processed feed stock to extract the dissolved components (mainly hemi-cellulose) which are discharged via conduit 48 to a blow-tank 28 or similar device. The sealing and extraction device may increase the pressure of the feed stock from the gauge pressure, e.g., 1.5 bar to 10 bar, at the discharge of the first reactor to the gauge pressure in the second reactor 16 of 8 bar to above 25 bar.

Figure 5:
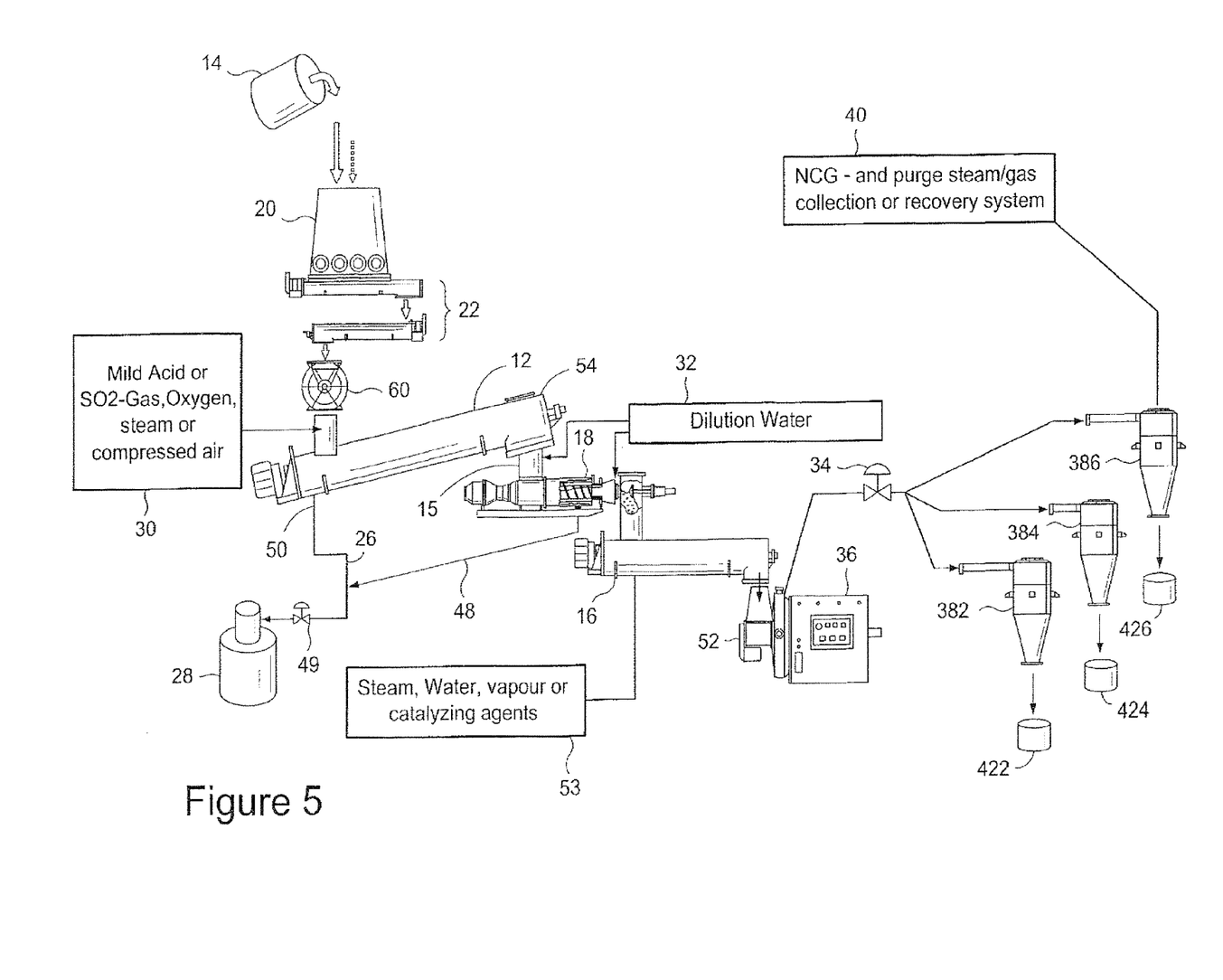
FIG. 5 depicts a reactor system with a plurality of cyclone separators.
Figure 6:
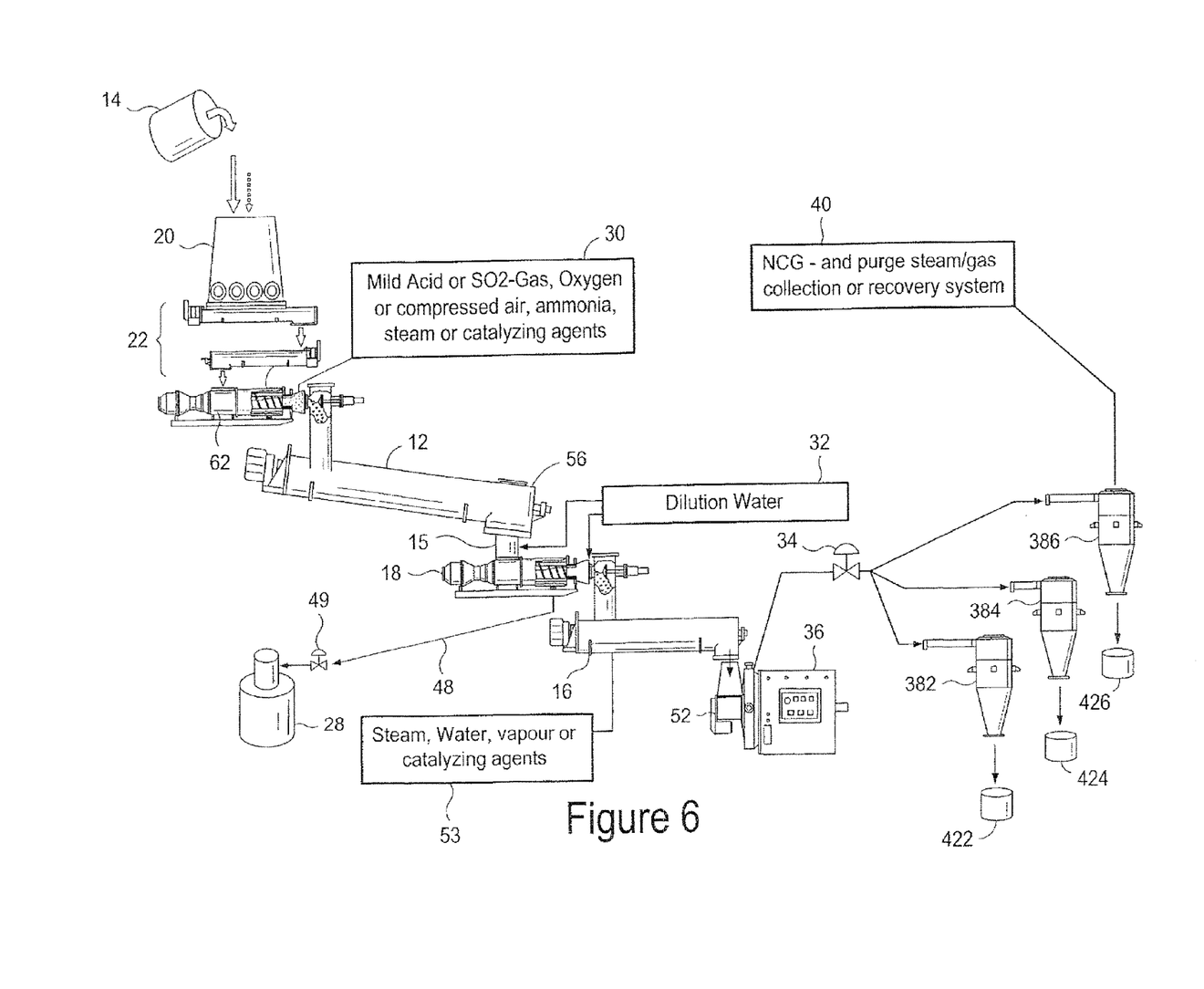
FIG. 6 depicts a reactor system with a plug screw feeder.
Figure 7:
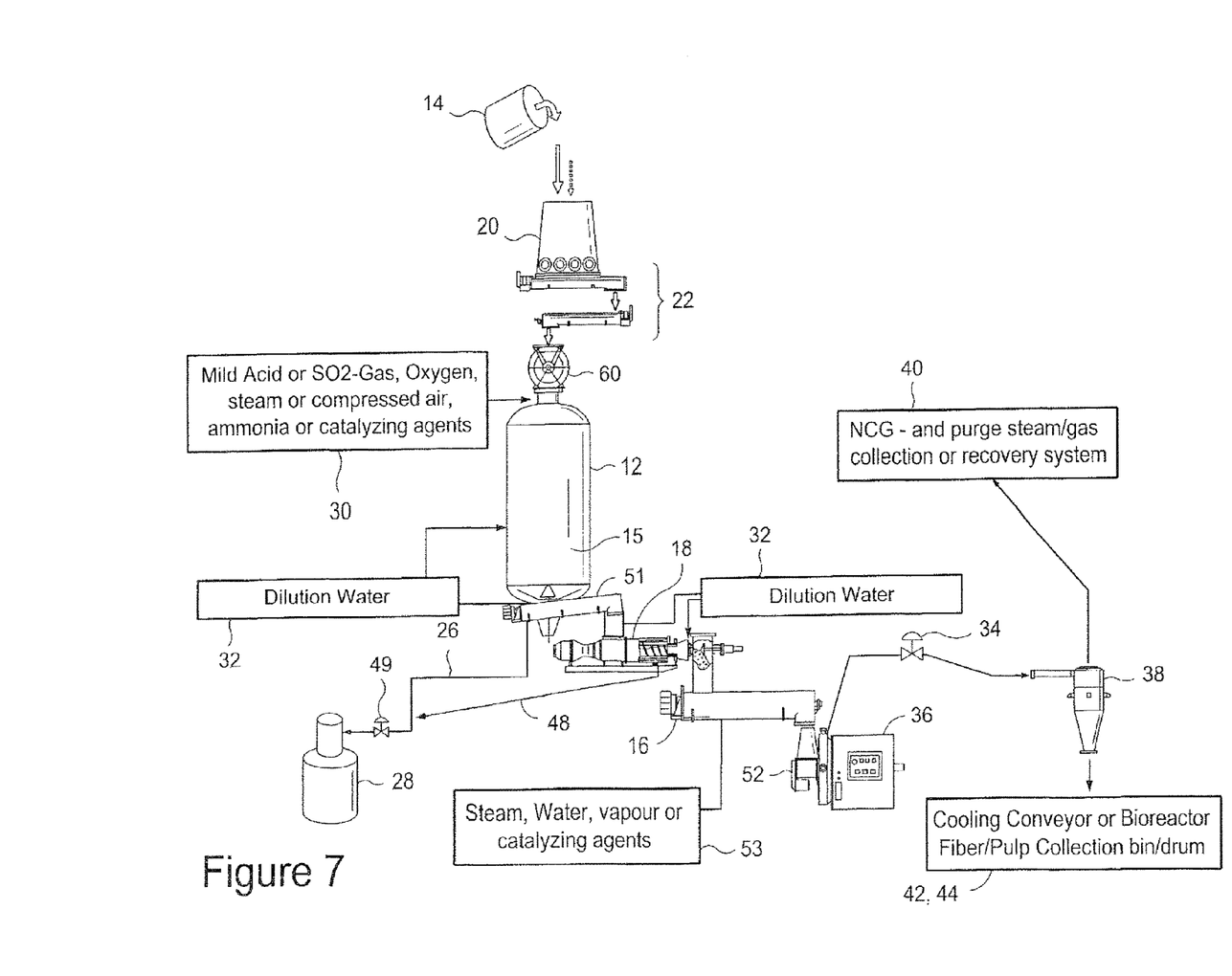
FIG. 7 depicts a reactor system with a vertical first reactor.

The pressurized feed stock may flow from the first reactor 12 to the sealing and extraction device 18 by the force of gravity, by the continuous flow of feed stock in the reactor (as is shown in FIGS. 2 to 6) or by a discharge scraper or a discharge screw 51 as is shown in FIG. 7. The extraction device 18 provides a pressured seal between the first and second pressurized reactors 12 and 16. Because the feed stock is discharged from the first reactor 12 under pressure, the sealing and extraction device 18 preferably has an inlet configured to receive feed stock under pressure. For example, the inlet to the sealing and extraction device 18 is sealed to the outlet of the first reactor 12 and does not release the pressure on the feed stock entering the device 18.

Figure 8:
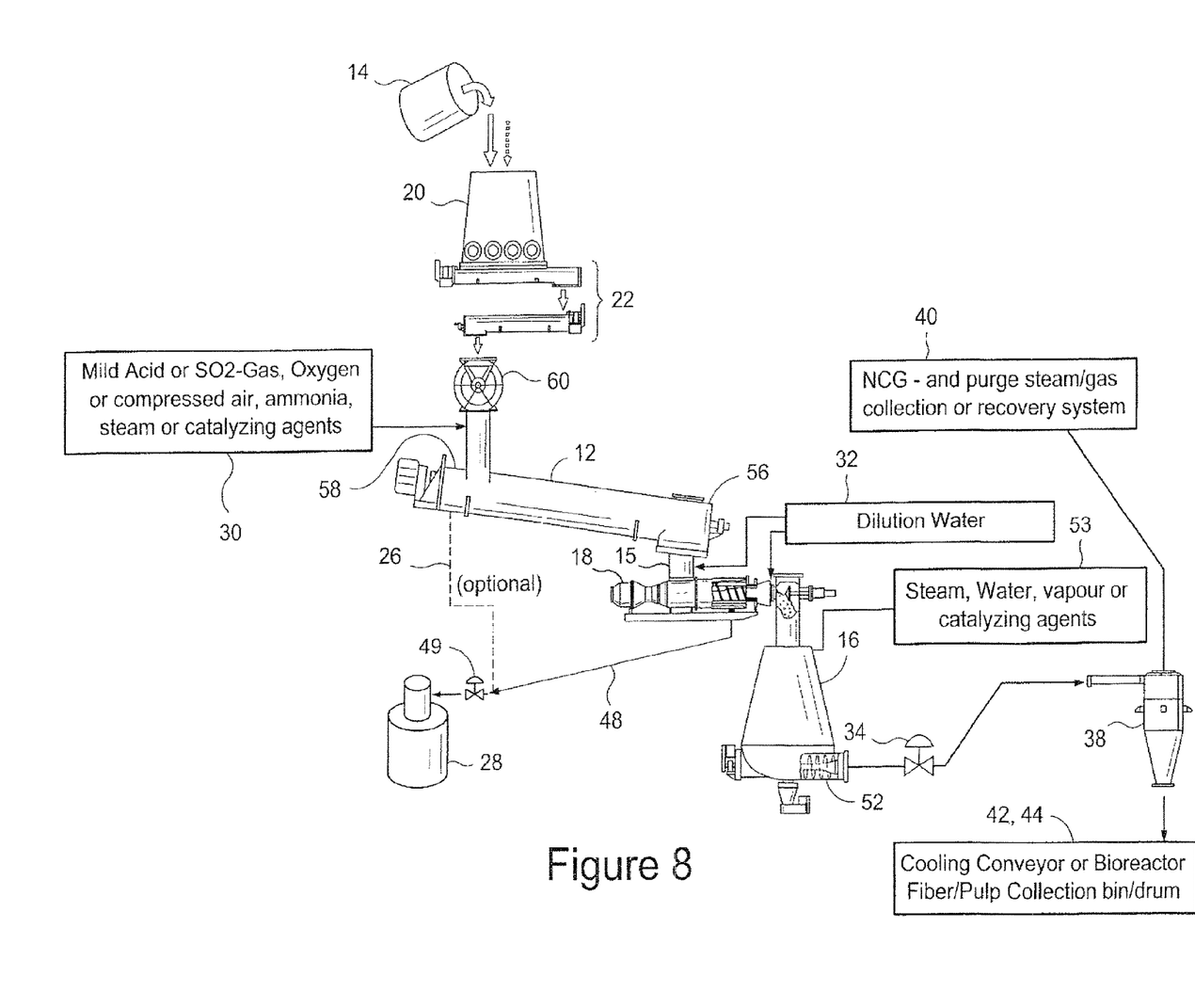
FIG. 8 depicts an alternative arrangement of a reactor system with a conical second reactor.

The second reactor 16 may be, for example, a vertical, horizontal or a conical reactor. Vertical reactors are shown in FIGS. 7 and 8 and may include a bottom section to promote the downward flow of feedstock, such as a diamondback section disclosed in U.S. Pat. Nos. 5,617,975 and 5,628,873, which are incorporated by reference. Suitable vessels for the second reactor 16 are conventional and are typically used in steam explosion pulping processes.

The second reactor is preferably operated at a higher pressure than the first reactor. From the second reactor assembly (which may include a second reactor 16 or a second reactor 16 and a reactor discharge device 36), the feed stock is discharged at high gauge pressures, such as between 8 bar to 25.5 bar. The second reactor assembly may include a discharge device 52, such as a discharge screw feeder that moves the feed stock to a reactor discharge device 36. The process 10 maintains the feed stock at a substantially high gauge pressure, e.g., above 1.5 bar, from the first reactor 12, through the sealing extraction device 18, the second reactor 16, the reactor discharge device 36 and to the blow-valve 34.

The second reactor 16 processes the cellulosic biomass feed stock at temperatures of, for example, 170° C. to 230° C. for approximately two to five minutes (or longer), and at a gauge pressure of eight (8) bar to 25.5 bar (800 kilopascals to 2,550 kilopascals). The second reactor 16 may include a steam phase in which steam is injected directly in the reactor to provide heat energy for the feedstock. In the second reactor 16, one or more of steam, vapor and liquid water from sources 53, 32 diffuses into the inner structure of ligno-cellulosic material of the feed stock. In addition, the sources of steam, water vapor or liquid water 53, 32 may provide other liquids such as a liquid source of catalyzing agents to be injected into the second pressurized reactor 16.

Water 32 may be directly injected into the second reactor 16 or the sealing and extraction device 18 to provide diluted water to be infused into the feed stock. The dilution water 32 and sources 53 of steam, vapor and catalyzing agents may be injected into the second reactor 16 at point(s) proximate to where the feedstock enters the reactor.

The steam or water vapor is infused into the feedstock in the second reactor 16. The steam and water vapor partially condense as liquid water in the capillary-like micro-porous structure of the inner structure of the lingo-cellulosic material being processed in the second reactor.

The pressure of the feed stock is reduced dramatically by passing through a blow-valve 34 downstream of the second reactor assembly. The pressure drop across the blow-valve 34 is preferably at least a ten (10) bar reduction in pressure. The pressure of the feed stock may be reduced by the blow-valve 34 to one to two bars gauge, wherein zero bar gauge is at substantially atmospheric air pressure. The large pressure drop across the valve 34 is suitable for steam explosion pulping. The rapid pressure drop, e.g., "flashing", converts to steam the condensed liquid water in the cells of the lingocellulosic material of the feed stock. The conversion to steam of the water in the cells of the feed stock causes a massive disruption, e.g., an "explosion", of the cells in the cellulosic biomass feed stock. The disruption occurs because the volume occupied by the steam is much greater than the volume occupied by the water in the cells. The massive disruption includes bursting individual cells of the feed stock and rupturing the fibers along amorphous cellulose, such as between the cylindrical tubes and fibers of the cellulosic structure of the feed stock.

The feed stock pressure at the discharge of the second reactor 16 may be sufficient for steam explosion pulping, as is shown in FIG. 8. Alternatively, a discharge device 36 may be included in the second reactor assembly to boost the pressure of the feed stock to above the pressure in the second reactor. The reactor discharge device 36 may further increase the pressure of the feed stock to a pressure suitable for steam explosion pulping, such as from 8 bar gauge to 25 bar gauge.

The second pressurized reactor 16 may discharge the feed stock under a high pressure to a reactor discharge device 36 between the second reactor and the blow-valve 34. The second pressurized reactor assembly may comprise the reactor 16 with or without a reactor discharge device 36. The reactor discharge device 36 may be, for example, one or more of a scraper or sweeper at the feedstock discharge port of the second reactor, a disc mill refiner, a medium density fiber board (MDF) disc refiner, a disc high pressure compressor or a discharge plug feeder. For example, an embodiment of the reactor discharge device 36 may be a single disc refiner operating at a rotational speed of 1,200 revolutions per minute (RPM) to 3,000 RPM driven by an electrical motor powered by 150 horsepower (110 kilowatts). The disc mill refiner embodiment of the reactor discharge device 36 may also partially refine the pressurized feed stock before the feed stock undergoes steam explosion reefing by passing through the blow valve 34.

During the steam explosion, the particles of the treated feed stock are separated from the cellulosic network of the feed stock. The cyclone separator or blow tank 38 includes a lower discharge 39 for particles and an upper vapor discharge 41 for the steam, non-condensable gases (NCG), compressible gases and other chemical vapors 40. These vapors 40, which may include volatile organic compounds (VOCs), may be recovered such as by passing the vapors through a heat exchanger to recover the heat energy in the vapor.

The separated particles of the treated feed stock discharged from the lower discharge 39 port of the cyclone or blow tank 38 may be cooled in a cooling device 42, which may include a belt or screw conveyor. The treated feed stock may be processed by further reactor(s) 44 that may apply acid or enzyme treatments to the treated feed stock. The treated feed stock is ultimately discharged as pre-treated feed stock 46.

The process 10 shown in FIG. 1 may be embodied in various configurations of reactors and other devices. Several embodiments of such configurations of reactors and other devices are shown in FIGS. 2 to 8. The reference numbers in FIGS. 2 to 8 that are common to FIG. 1 refer to devices performing same function identified by the common reference number in FIG. 1.

As shown in FIGS. 2 to 8, the first reactor 12, e.g., a pre-hydrolysis reactor, may be: inclined as shown in FIGS. 2 to 8; arranged vertically as shown in FIG. 9, or arranged substantially horizontal as shown in FIG. 10.

The first pressurized reactor 12 may be a conventional reactor such as a pandia-type reactor having an internal auger or screw to move feed stock through the reactor. The feed stock may enter the first reactor 12 through a pressure sealing device 24 (in FIG. 1) which may be a rotary valve 60 (such as shown in FIGS. 2, 4, 5, 7 and 8), a plug screen feeder 62, e.g., a MSD Impressafiner® (such as shown in FIGS. 3 and 6) or other feed system that introduces unpressurized feed stock to a pressurized reactor.

Figure 3:
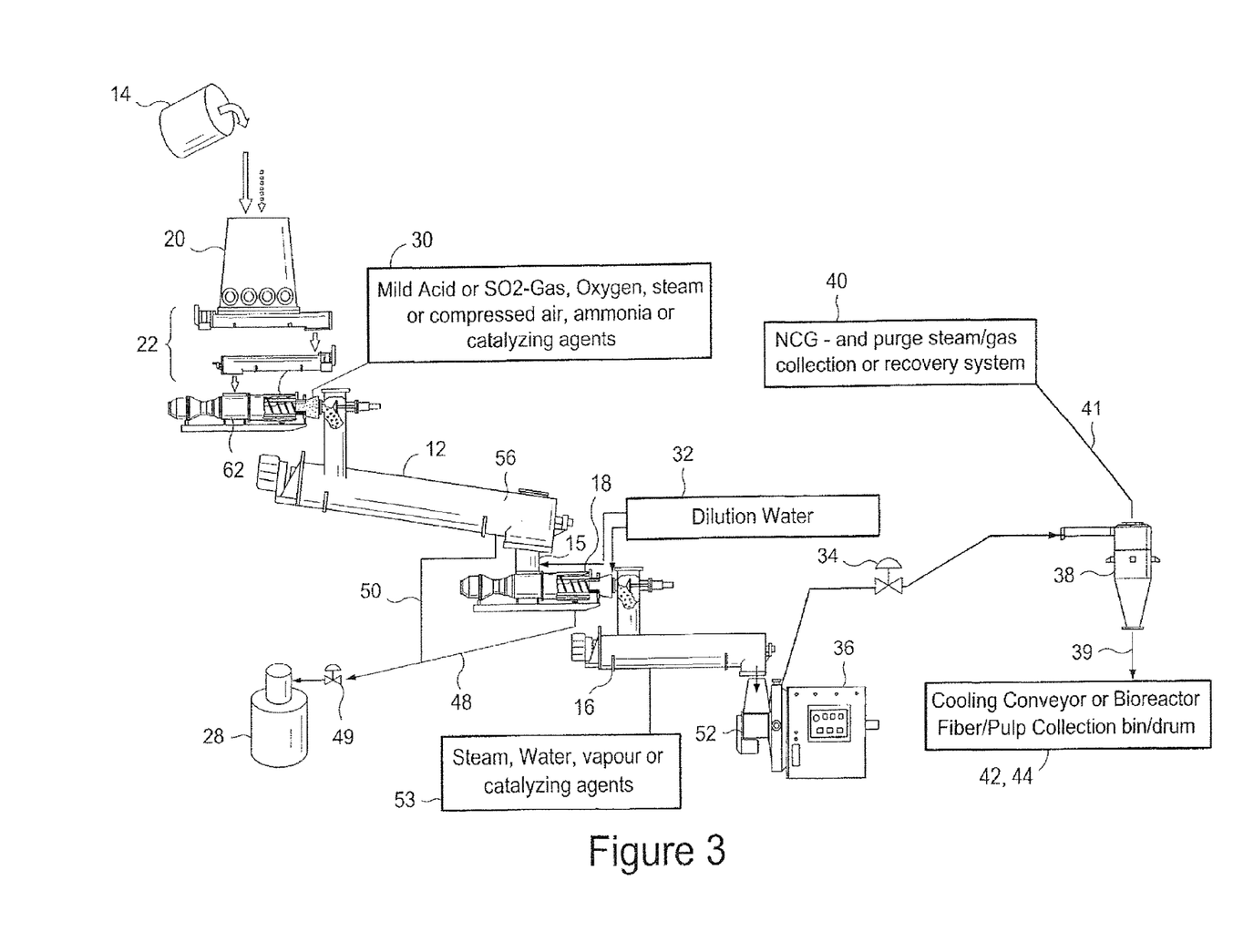
FIG. 3 depicts a reactor system with an inclined first reactor with an input higher than the discharge and a horizontal second reactor.
Figure 4:
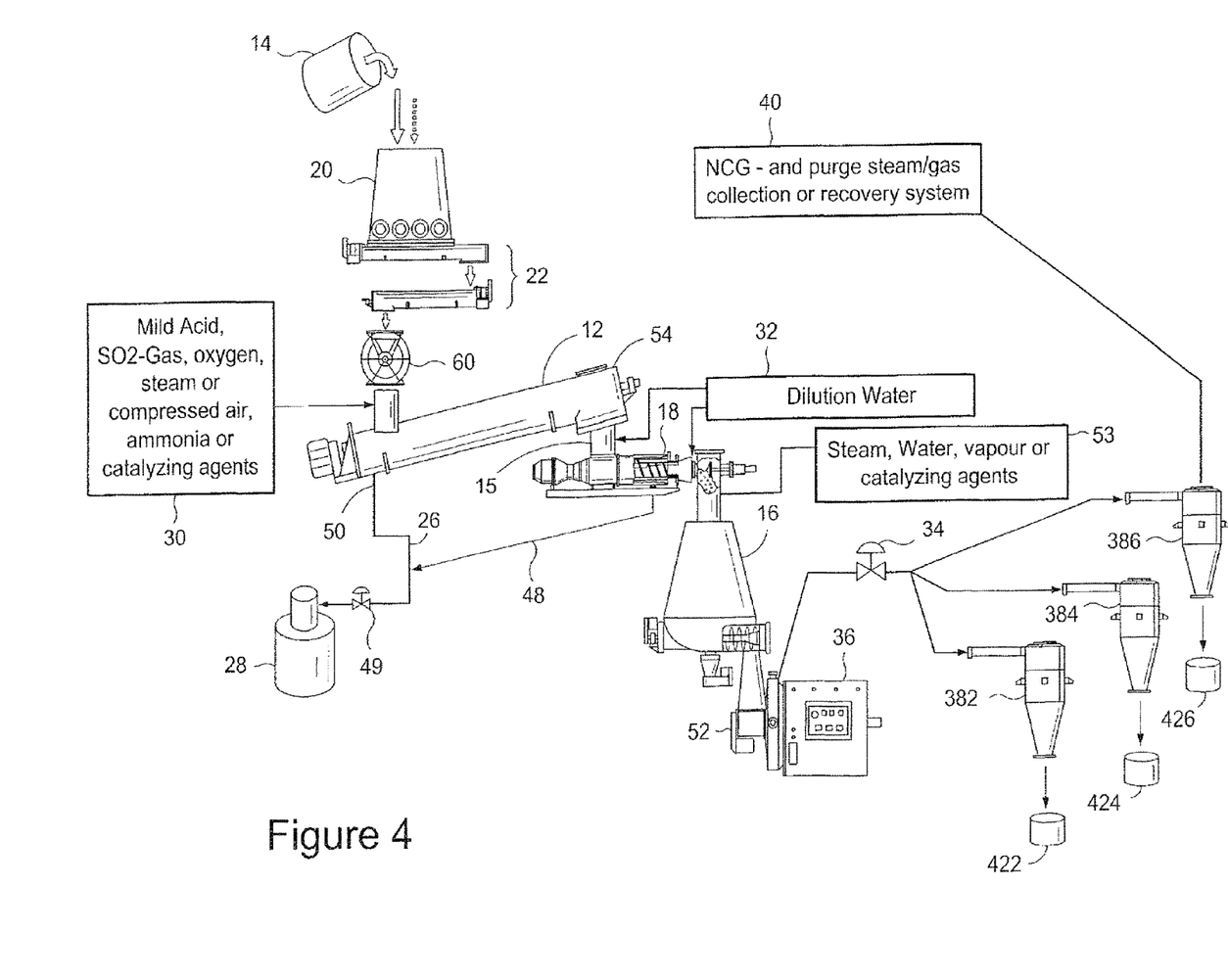
FIG. 4 depicts a reactor system with a conical second reactor.

The dissolved hemi-cellulose discharged from the reactor 12 may drain into the conduit 26 (as shown in FIGS. 2, 4, 6 and 7) or drain entirely into the pressurized sealing and extraction device 18 (as show in FIGS. 3 and 5). As shown in FIGS. 2, 3, 4 and 5, the inclined first reactors 12 with the lower end 50 opposite to an upper end 54 which discharging the feed stock will drain most or all of the dissolved hemi-cellulose, e.g., C5-sugars, as a liquid at a lower end 50 of the reactor. The upper end 54 of these inclined first reactors has a pressure maintaining coupling to the pressurized sealing device 18, which may be a plug screw feeder. Additional liquor having the dissolved hemi-cellulose may be extracted from the sealing device 18 and directed via conduits 48 and 26 to the reduction valve 49 and to the blow tank or drum 28. As shown in FIG. 3, the first reactor 12 may be inclined such that the lower end 56 of the reactor vessel has a pressure maintaining coupling to the pressurized sealing device. The lower end 56 of the reactors 12 shown in FIG. 3 discharges feed stock and the entirety of the liquid hemi-cellulose material to the pressure sealing device 18. A conduit 48 drains the liquid hemi-cellulose from the pressure sealing and extraction device 18 and directs the liquid to the pressure reduction valve 49 and tank or drum 28.

FIGS. 4 to 6 show that the feed stock, after passing through the blow valve 34 and being treated by steam explosion, may be separated into different flows each having a different cyclone separator 382, 384 and 386 and different discharge devices and further reactors 422, 424, 426. For example, a portion of the cellulose from the feed stock may be retained to be separated and processed separately for pulp (paper) or special chemicals applications.

The inclined first pressurized reactor 12 shown in FIG. 8 has a lower end 56 coupled to the pressurized seal 18. The upper end 58 of the reactor may have an optional drain conduit 26 that allows the hemi-cellulose liquid to flow from the reactor to the reduction valve 49 and tank 28.

The vertical first pressured reactor 12, shown in FIG. 7, includes a feed stock sweeper and conveyor 51 that discharges the feed stock from the reactor vessel and drains the hemi-cellulose liquid to the conduit 26 that directs the liquid through the reduction valve 49 and to the blow tank or drum.

A benefit of an embodiment of the cellulosic biomass feed stock pre-treatment process 10 is that the reactor vessels are preferably of constant or expanding cross-sections to allow for an expansion of the feedstock flow volume or flow rate without concern as to varying cross-sectional loading, channeling or clogging of the reactor vessels. For example, each of the reactor vessels 12, 16 may be oriented vertically, inclined and horizontal. Similarly, the reactors feedstock flow through the each of reactors may be downwards, upwards or horizontal depending on the orientation of the reactor vessel.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for pretreating cellulosic biomass feed stock comprising:
   pretreating the feed stock in a first pressurized reactor, wherein the feed stock undergoes hydrolysis in the first pressurized reactor, wherein the feed stock in the first pressurized reactor is under a gauge pressure of at least 1.5 bar;
   transferring the feed stock from the first pressurized reactor to a pressurized sealing device, wherein the feed stock in the pressurized sealing device is under a gauge pressure of at least 1.5 bar;
   maintaining a vapor phase in the first pressurized reactor by injecting steam into the first pressurized reactor, wherein the injected steam provides heat energy to the feedstock in the first pressurized reactor;
   washing the feed stock in a downstream region of the first pressurized reactor or in the pressurized sealing device;
   draining a liquid including dissolved hemi-cellulosic material extracted from the feed stock from at least one of the first pressurized reactor and the pressurized sealing device;
   discharging the feed stock from the pressurized sealing device through a second pressurized coupling to a second pressurized reactor, wherein the feed stock is maintained at a higher pressure in the second pressurized reactor than in the first pressurized reactor;
   in the second pressurized reactor, infusing cells of the feed stock with steam or water vapor by injecting steam or water vapor into the second pressurized reactor, and
   rapidly releasing a pressure applied to the feed stock infused with water to cause steam expansion in the cells of the feed stock and refine the feed stock.

2. The method of claim 1 further comprising introducing at least one of mild acid, sulfur dioxide gas ($SO_2$), oxygen, compressed air, steam, water and catalyzing agents to the feed stock in at least one of the first pressurized reactor and the second pressurized reactor.

3. The method of claim 1 wherein the step of pretreating the feed stock occurs in the first pressurized reactor having an internal temperature in a range of 110 degrees Celsius to 160 degrees Celsius, and a pressure in a range of 150 kilopascals to 600 kilopascals, and wherein the feed stock remains in the first pressurized reactor for a period of ten minutes to sixty minutes.

4. The method of claim 1 wherein the step of pretreating the feed stock occurs in the first pressurized reactor having an internal temperature in a range of 110 degrees Celsius to 175 degrees Celsius, and a pressure in a range of 150 kilopascals to 1000 kilopascals, and wherein the feed stock remains in the first pressurized reactor for a period of ten minutes to sixty minutes, and the feed stock in the pressurized sealing device is under a pressure in a range of 150 kilopascals to 1000 kilopascals.

5. The method of claim 1 wherein the feed stock flows as a continuous stream through the first pressurized reactor, the pressurized sealing device, the second pressurized reactor and to the rapid release of pressure downstream of the second pressurized reactor, and the feed stock in the pressurized sealing device is under a pressure in a range of 150 kilopascals to 1000 kilopascals.

6. The method of claim 1 wherein the rapid release of pressure reduces the pressure of the feed stock by at least ten bar.

7. The method of claim 1 wherein the washing step is between said transferring step and said draining step and washes the dissolved hemi-cellulosic material from said feedstock between said first pressurized reactor and said second pressurized reactor.

8. The method of claim 1 wherein said washing step is performed at a temperature below 160° C.

9. The method of claim 1 wherein said washing step is performed at a temperature below 140° C.

10. The method of claim 1 wherein the infusion of the steam or the water vapor into the second reactor forms a vapor phase in the second pressurized reactor.

11. A method including:
    pretreating biomass feed stock in a first pressurized reactor, wherein the feed stock undergoes hydrolysis in the first pressurized reactor;
    discharging the feed stock from the first pressurized reactor to a pressurized sealing device having a first pressurized coupling to a feedstock discharge port of the first pressurized reactor;
    maintaining a vapor phase in the first pressurized reactor by injecting steam into the first pressurized reactor;
    washing the feed stock in or downstream of the first pressurized reactor;
    draining dissolved hemi-cellulosic material extracted from the feed stock;
    discharging the feed stock from the pressurized sealing device through a second pressurized coupling to a second pressurized reactor;
    in the second pressurized reactor, infusing cells of the feed stock with steam or water vapor;
    maintaining the feed stock under a pressure of at least 150 kilopascals as the feed stock moves through the first pressurized reactor, from the first pressurized reactor to the second pressurized reactor, and through the second pressurized reactor, and
    subjecting the feed stock with the infused cells to a rapid pressure release to cause expand and burst the cells of the feed stock.

12. The method of claim 11 further comprising introducing at least one of mild acid, sulfur dioxide gas ($SO_2$), oxygen, compressed air, steam, water and catalyzing agents to the feed stock in at least one of the first pressurized reactor and the second pressurized reactor.

13. The method of claim 11 wherein the step of pretreating the feed stock occurs in the first pressurized reactor having an internal temperature in a range of 110 degrees Celsius to 160 degrees Celsius, and a pressure in a range of 150 kilopascals to 600 kilopascals, and wherein the feed stock remains in the first pressurized reactor for a period of ten minutes to sixty minutes.

14. The method of claim 11 wherein the step of pretreating the feed stock occurs in the first pressurized reactor having an internal temperature in a range of 110 degrees Celsius to 175 degrees Celsius, and a pressure in a range of 150 kilopascals to 1000 kilopascals, and wherein the feed stock remains in the first pressurized reactor for a period of ten minutes to sixty minutes.

15. The method of claim 11 wherein the feed stock flows as a continuous stream through the first pressurized reactor, the pressurized sealing device, the second pressurized reactor and to the rapid release of pressure downstream of the second pressurized reactor.

16. The method of claim 11 wherein the rapid release of pressure reduces the pressure of the feed stock by at least ten bar.

17. The method of claim 11 wherein the washing step is performed between said discharging step and draining step and washes the dissolved hemi-cellulosic material from said feedstock between said first pressurized reactor and said second pressurized reactor.

18. The method of claim 11 wherein said washing step is performed at a temperature below 160° C.

19. The method of claim 11 wherein said washing step is performed at a temperature below 140° C.

20. The process of claim 11 wherein the feedstock flows through said first and said second pressurized reactor as a continuous flow.

21. The process of claim 11 wherein the injection of the steam or the water vapor into the second reactor forms a vapor phase in the second pressurized reactor.

* * * * *